Figure 1:
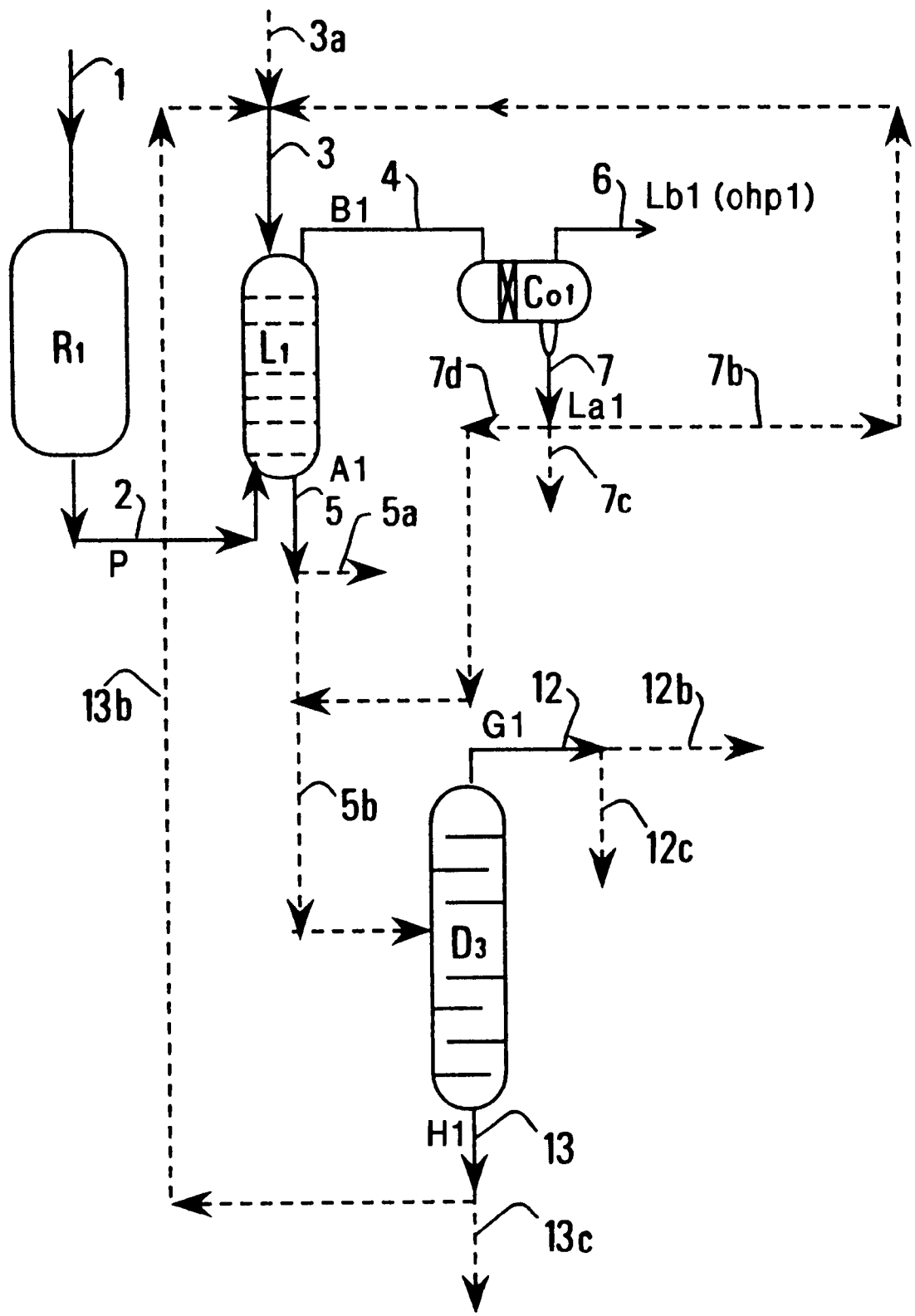

United States Patent [19]
Marion et al.

[11] Patent Number: 6,072,095
[45] Date of Patent: *Jun. 6, 2000

[54] PROCESS FOR PRODUCING A TERTIARY OLEFIN BY DECOMPOSING A TERTIARY ALKYLETHER, COMPRISING A FIRST STEP OF PURIFICATION BY WASHING WITH WATER

[75] Inventors: Marie-Claire Marion, 69100 Villeurbanne; Vincent Coupard, 69002 Lyon; Alain Forestière, 69390 Vernaison; Philippe Travers, 92500 Rueil Malmaison; Jean-Charles Viltard, 26000 Valence, all of France

[73] Assignee: Institut Francais Du Petrole, Rueil-Malmaison Cedex, France

[ * ] Notice: This patent is subject to a terminal disclaimer.

[21] Appl. No.: 09/030,916

[22] Filed: Feb. 26, 1998

[30] Foreign Application Priority Data

Feb. 26, 1997 [FR] France .................................. 97 02390

[51] Int. Cl.⁷ ...................................................... C07C 1/00
[52] U.S. Cl. ............................ 585/639; 585/640; 585/642
[58] Field of Search .................................... 585/638, 639, 585/640, 642

[56] References Cited

U.S. PATENT DOCUMENTS 4,447,668  5/1984  Smith, Jr. et al. ........................ 585/639

*Primary Examiner*—Bekir L. Yildirim
*Attorney, Agent, or Firm*—Millen, White, Zelano & Branigan, P.C.

[57] ABSTRACT

A process for producing a tertiary olefin by decomposing an ether comprises a) decomposing an ether to a product containing an alcohol and a tertiary olefin, b) purifying at least a portion of the product from a) in a water washing extraction zone (L1) to obtain an aqueous fraction (A1) containing the major portion of the alcohol and a fraction (B1) containing the major portion of the tertiary olefin, the fraction (B1) containing the tertiary olefin, water, possibly ether and light compounds and being substantially free of alcohol, and c) in which at least a portion of the fraction (B1) from b) is sent to a separation zone (Co1) from which a liquid aqueous fraction (La1) and a liquid fraction (Lb1) containing the major portion of the tertiary olefin, possibly ether and possibly light compounds, are recovered.

31 Claims, 7 Drawing Sheets

PROCESS FOR PRODUCING A TERTIARY OLEFIN BY DECOMPOSING A TERTIARY ALKYLETHER, COMPRISING A FIRST STEP OF PURIFICATION BY WASHING WITH WATER

The invention relates to a process for decomposing tertiary alkyl ether(s) to produce high purity tertiary olefin (s). In particular, it relates to a process for the production of very high purity isobutene and methanol from methyl-tertio-butyl-ether (MTBE). The process of the present invention is applicable to the synthesis of any tertiary olefin from a tertiary alkyl ether [for example ETBE (ethyl-tertio-butyl-ether), ETAE (tertio-amyl-methyl-ether), TAME (tertio-amyl-methyl-ether, and isopropyl-tertio-butyl-ether]. The remainder of the description, in particular the operating conditions in each zone, is given by way of indication for the synthesis of isobutene from MTBE.

A variety of routes for producing high purity isobutene can be employed industrially. The oldest is the sulphuric acid extraction process, but it is expensive and obsolete; it is known to be a contaminating process as waste acid is discharged. Further, the isobutene yield does not exceed 90%. The company ARCO uses tertio-butyl alcohol (TBA) dehydration, TBA being a by-product obtained from their propylene oxide production process. The isobutane dehydrogenation process was developed during the last few years as a result of the large and increasing demand for MTBE. However, that process can only be profitable with very large production capacities.

High purity isobutene production from cracking MTBE is as suitable for small capacities as for large capacities. Further, such a route benefits from the infrastructure generated by the increasing importance of ethers in reformulated gasoline. A number of refineries throughout the world have MTBE production installations, for example. Further, there is a global exchange market for MTBE. This means that the production of high purity isobutene from MTBE can readily be carried out anywhere in the world, in and remote from refineries.

The concept of producing isobutene by decomposing an ether, more particularly MTBE, has long been known, but prior art processes have suffered from certain disadvantages.

In the process developed by SUMITOMO described, for example, in European patent application EP-A-0 068 785, the MTBE decomposition reaction is carried out in the liquid phase, in the presence of a solid acid catalyst which is an ion exchange resin. Two product streams are obtained: isobutene and methanol. As described, isobutene is obtained directly overhead from a distillation column with no other purification step. The isobutene obtained contains a certain number of impurities, beginning with a small fraction of methanol which is azeotropically distilled from dimethylether (DME), which is a volatile compound formed by condensing methanol in the presence of an acid catalyst. It is probable that the purity of the isobutene is insufficient for use in, for example, the production of polyisobutene or other copolymers. Further, there is no apparent way of avoiding the accumulation of heavy impurities such as dimers of isobutene or methyl sec-butyl ether (MSBE), which in the long run results in a fatal reduction of product purity.

In the process developed by ERDOLCHEMIE, described in United States patent U.S. Pat. No. 4,409,421, for example, isobutene is purified by eliminating residual alcohol entrained with the tertiary olefin by adsorption. This method has the disadvantage of requiring regular regeneration of the adsorbent. Further, the problem of recovery of the major portion of the alcohol from the decomposition step is not solved.

More recently in U.S. Pat. No. 5,095,164, the same company has described carrying out the decomposition reaction in a distillation apparatus. The catalyst is placed in the bottom of the column at the reboiler level. That particular implementation limits the reaction temperature, which is directly imposed by the nature of the ether and the operating pressure. Further, it apparently encourages the formation of reaction by-products such as the formation of dimers of isobutene and/or dimethylether formation. In this regard, the quality and/or development of the products is not clearly explained.

In U.S. Pat. No. 4,287,379, BASF describes a scheme which integrates both ether synthesis, its separation then the ether decomposition step to produce the isobutene. However, in order to avoid certain purification steps, etherification is carried out with a $C_3$ or $C_4$ alcohol, which is a major disadvantage as regards the international MTBE market.

Finally, we can cite the two schemes of the SNAMPROGETTI process presented in "Chemical Economy & Engineering Review", vol. 14, n° 6, June 1982, including both the MTBE synthesis step and the MTBE decomposition step for the production isobutene. Such schemes use a zone for fractionation by distillation immediately after the reactional decomposition zone. Since the treated product is rich in methanol, fractionation results in the production of two effluents each containing the alcohol: in the overhead effluent, the alcohol is entrained azeotropically, and in the bottoms effluent the majority of the alcohol obtained in the ether decomposition step is obtained. In such a scheme, alcohol recovery is thus complicated since it must be recovered both from the overhead effluent from the fractionation column and from the bottoms effluent from that column.

In the description in Rumanian patent application RO 105 954, the decomposition step takes place in an adiabatic reactor in the presence of steam. The presence of water in the reaction medium is deleterious to the selectivity of the decomposition reaction as isobutene is lost by reaction with water to form tertio-butyl alcohol (TBA). Further, the system also requires the provision of a supplementary decanting step. In addition, the alcohol recovery column (column C2 in the figure in that patent) is enormous due to the quantities of water used.

International patent application WO 91/01804 principally describes the possibility of regenerating the catalyst, which is preferably a clay. Thus the ether and or alcohol extracted during the washing step is returned to the reaction section to be used as a regeneration stream. Such a batch operation, which alternates the reaction period and regeneration period at a steady frequency, results from using a catalyst which is not stable over time. The single example given concerns the decomposition of tertio-amyl-methyl-ether (TAME) to form isoamylenes, a reaction which is less demanding as regards temperature than MTBE decomposition with respect to the position of the thermodynamic equilibrium.

Thus there are difficulties in operation and also difficulties in inserting it into a generally integrated scheme where neighbouring units operate continuously (for example the etherification unit for synthesis of MTBE or TAME). It is thus necessary to store products upstream and downstream, involving additional costs and constant management.

The process of the invention can overcome the above disadvantages of the systems described in the prior art publications cited above. It concerns a process for the production of tertiary olefin(s) from a tertiary alkyl ether, characterized by a very high purity, and its implementation.

The invention concerns a process for decomposing tertiary alkyl ether(s), in particular those defined above, preferably MTBE or ETBE, to produce high purity tertiary olefin(s), in particular isobutene. When decomposing other ethers, a mixture can be obtained which contains a plurality of tertiary olefins. Thus in the case of TAME decomposition, a mixture containing 9-methyl-1-butene and 2-methyl-2-butene is obtained.

In addition to the reaction zone itself, the process of the invention comprises zones for purification, recovery or recycling the various products to optimise upgrading of the products used and to minimise losses.

FIGS. 1 to 7 are flowcharts each illustrating one of the multiple variations of the process of the present invention. The dotted lines show the various possible options, namely recycling options and optional apparatus in the variation under consideration. The process of the present invention is described with reference to these figures with the aim of facilitating comprehension. In the figures, similar means are designated by the same reference letters and numbers. They should not be considered to limit the invention and other variations which are not illustrated form an integral part of the present invention provided that they follow from the description in obvious fashion. FIG. 1 illustrates the most general form of the process of the invention and is described below.

The present invention provides a process for producing a tertiary olefin by decomposing a tertiary alkyl ether, comprising:

a) a step a) for decomposing at least one tertiary alkyl ether in a reaction zone comprising at least one reactor (R1) containing a catalyst for decomposing said ether, said step being carried out under conditions which can at least partially decompose said tertiary alkyl ether to a product (P) containing at least one alcohol and at least one tertiary olefin and possibly ether which is not decomposed in this step a) and possibly light compounds, generally initially contained in the product from step a);

b) a step b) for purifying at least a portion of product (P), preferably all of the product, in a water washing extraction zone (L1) from which an aqueous fraction (A1) containing the major portion of the alcohol initially present in said portion and a fraction (B1) containing the major portion of the tertiary olefin initially present in said portion are obtained, said fraction (B1) containing said tertiary olefin, water, possibly ether and possibly light compounds and being substantially free of alcohol or containing a very small proportion thereof (for example less than 10%, normally less than 5% and usually less than 2% by weight);

said process being characterized in that it comprises a step c) in which at least a portion of fraction (B1) from step b) is sent to a separation zone (Co1), preferably comprising at least one coalescing means or coalescer, from which a liquid aqueous fraction (La1) and a liquid organic fraction (Lb1) containing the major portion of the tertiary olefin initially present in said portion of the fraction (B1) are recovered, said fraction (Lb1) containing said tertiary olefin and possibly ether and possibly light compounds.

This implementation of the present invention is illustrated in FIG. 1. The feed containing the ether(s) to be decomposed is introduced via line 1 into a reactor (R1) containing an ether decomposition catalyst. A product (P) containing at least one alcohol and at least one tertiary olefin and possibly ether which has not decomposed in step a) and possibly light compounds is recovered via line 2 and sent to water washing extraction zone (L1) into which water for washing is introduced via line 3. An aqueous fraction (A1) containing water and the major portion of the alcohol initially present in product (P) is obtained from this water washing extraction zone (L1) via line 5, and a fraction (B1) containing the major portion of the tertiary olefin initially present in product (P) is recovered via line 4, fraction (B1) containing the tertiary olefin, water, possibly ether which has not decomposed in step a) and possibly light compounds and being essentially free of alcohol. This fraction (B1) is introduced via line 4 into a coalescer (Co1) of step c) from which an essentially aqueous fraction (La1) is recovered via line 7 and an organic fraction (Lb1) containing purified tertiary olefin (Ohp1) is recovered via line 6.

Within the scope of the present invention, aqueous fraction (A1) can be recovered as it is for sending to a water treatment section or it can be split into an aqueous fraction which is depleted in alcohol, reusable, for example, as washing water or it can be sent to a water treatment section, and an organic fraction which is enriched in alcohol which can, for example, be recovered and sent to a zone for synthesising ether by reaction between an olefin and an alcohol.

The process of the invention may comprise a number of variations which an in particular improve the quality of the recovered tertiary olefin and which are described below. These variations can be implemented separately or simultaneously, either in their totality or in combinations of two or more.

In one variation, the process of the present invention (see FIG. 1 in particular) comprises at least partial recycling of the liquid fraction (La1) obtained from step c) to the water extraction zone (L1) via lines 7, 7b and 3. The whole of the fraction (La1) obtained from step c) can be recycled to the water extraction zone (L1) of step b). When recycling is partial or non existent, part or all of the aqueous fraction (La1) can be sent to a waste water treatment zone, for example, via lines 7 and 7c.

In a further variation, the process of the present invention comprises a step f) (see FIGS. 1, 3, 5, 6 and 7 in particular) in which at least a portion, or all, of fraction (A1) from step b) from line 5 is sent via line 5b in FIG. 1 to a fractionation zone (D3) from which a fraction (G1) containing the major portion of the alcohol initially present in the portion is recovered via line 12 and an aqueous fraction (H1) which is free of the major portion of the alcohol initially present in the portion is recovered via line 13. In this implementation, at least a portion of fraction (G1) obtained from step f) containing alcohol can be sent via line 12c to a zone for synthesising ether by reaction between at least one tertiary olefin and at least one alcohol. It is also possible to send all of this alcohol to the ether synthesis zone. It is also possible to recover all or part of this alcohol via line 12b for other uses. It is also possible to recycle at least a portion, or all, of the aqueous fraction (H1) via lines 13b and 3 to water washing extraction zone (L1) in step b). When recycling is partial or non existent, part or all of the aqueous fraction (H1) can, for example, be sent to a waste water treatment zone via line 13c.

In a further variation of the process of the invention (see FIG. 1 in particular), at least a portion of the liquid fraction (La1) obtained from step c) is sent via lines 7, 7d and 5b to the fractionation zone (D3) of step f) in the above variations where water is recycled to zone (L1) either from the fraction (La1) from step c) or from aqueous fraction (H1) from step f), or from both of these fractions, the quantity of water used in extraction zone (L1) is adjusted if necessary using at least one means for introducing makeup water into zone (L1) via lines 3a and 3 (see FIGS. 1, 3, 5, 6, 7 in particular). This makeup of water can compensate for loss of water by entrainment or due to saturation of the treated hydrocarbon stream, and can also replace any water which may have been purged.

In a further variation, the process of the present invention comprises a step d) (see, in particular, FIGS. 2 to 7) in which at least a portion of the liquid organic fraction (Lb1) (containing purified tertiary olefin (Ohp1)) from step c), preferably all of that fraction, is sent via line 6 to a fractionation zone (D1) from which a fraction (E1) containing the major portion of the ether initially contained in the portion is recovered via line 9 and an organic fraction (F1) containing the major portion of the tertiary olefin initially contained in that portion and possibly light compounds is recovered via line 8. Fraction (F1) contains purified tertiary olefin (Ohp2). In this implementation, at least a portion, preferably all, of fraction (E1) is recycled to zone (R1) via line 9b. When recycling is partial or non existent, this portion of fraction (E1) can, for example, be sent to a gasoline pool or storage zone via line 9c.

In a further variation, the process of the present invention comprises a step e) (see FIGS. 2 and 3 in particular) in which at least a portion of fraction (F1) from step d), preferably all of that fraction, is sent via line 9 to a fractionation zone (D2) from which a fraction (Lg1) containing the majority of the light compounds initially present in that portion is recovered via line 10 and a fraction (Ohp3) containing the majority of the tertiary olefin initially contained in that portion is recovered via line 11. Fraction (Ohp3) essentially contains purified tertiary olefin.

In a still further variation (see FIGS. 4 and 5 in particular), the process of the present invention comprises a step g) in which at least a portion of fraction (F1) from step d), preferably all of that fraction, is sent via line 8 to a water washing extraction (L2) from which an aqueous fraction (A2) containing the major portion of the alcohol initially present in that portion is obtained via line 16, and a fraction (B2) containing the major portion of the tertiary olefin initially present in that portion is obtained via line 15, fraction (B2) containing the purified tertiary olefin (Ohp4), water, and possibly light compounds and being substantially free of alcohol.

In a further variation (see FIGS. 4 and 5 in particular), the process of the present invention comprises a step h) in which at least a portion of fraction (B2) from step g), preferably all of that fraction, is sent via line 15 to a fractionation zone (D2) from which a fraction (Lg2) containing the majority of the light compounds initially present in that portion is recovered via line 10 and a fraction (Ohp5) containing the majority of the tertiary olefin initially contained in that portion is recovered via line 11. Fraction (Ohp5) essentially contains purified tertiary olefin.

In a further variation (see FIG. 4 in particular) the process of the present invention comprises a step i) in which at least a portion of the aqueous fraction (A2) from step g), preferably all of that fraction, is sent via lines 16 and 16b to a fractionation zone (D4) from which a fraction (G2) containing the major portion of the alcohol initially present in that portion is recovered via line 17 and an aqueous fraction (H2) which is free of the major portion of the alcohol initially present in that portion is recovered via line 18. In this implementation, at least a portion of fraction (G2) from step i) and containing alcohol can be sent via line 17c to a zone for synthesising ether by reaction between at least one tertiary olefin and at least one alcohol. It is also possible to send all of this alcohol to the ether synthesis zone. Part or all of this alcohol can also be recovered via line 17b for other uses. It is also possible to recycle at least part, or all, of the aqueous fraction to (H2) to water extraction zone (L2) of step g) via lines 11b and 14 and/or to water extraction zone (L1) of step b) (not shown in FIG. 4). Thus at least a portion of the aqueous fraction (H2) is recycled to at least one water extraction zone (L1) and/or (L2). When recycling is partial or non existent, this portion of the aqueous fraction (H2) can, for example, be sent via line 18c to a waste water treatment zone.

In a still further variation (see FIG. 5 in particular) of the process of the present invention, at least a portion of fraction (A2) from step g), preferably all of that fraction, is sent to extraction zone (L1) via lines 16, 16c and 3.

In a yet still further variation (see FIG. 5 in particular) of the process of the present invention, step f) is carried out and at least a portion of the fraction (A2) from step g) is sent via lines 16, 16b and 16d to fractionation zone (D3) described above in connection with step f).

Figure 5:
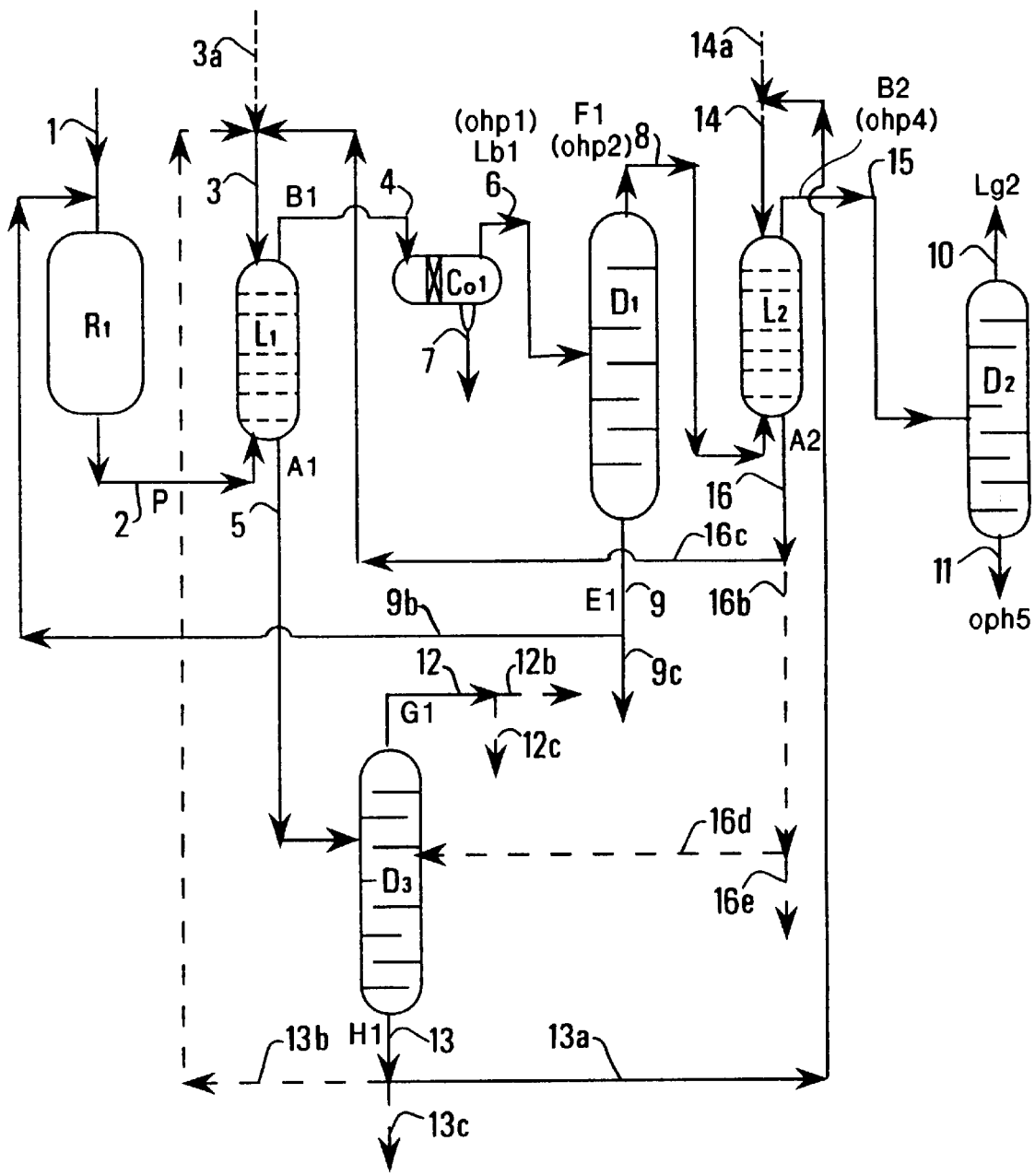
Figure 6:
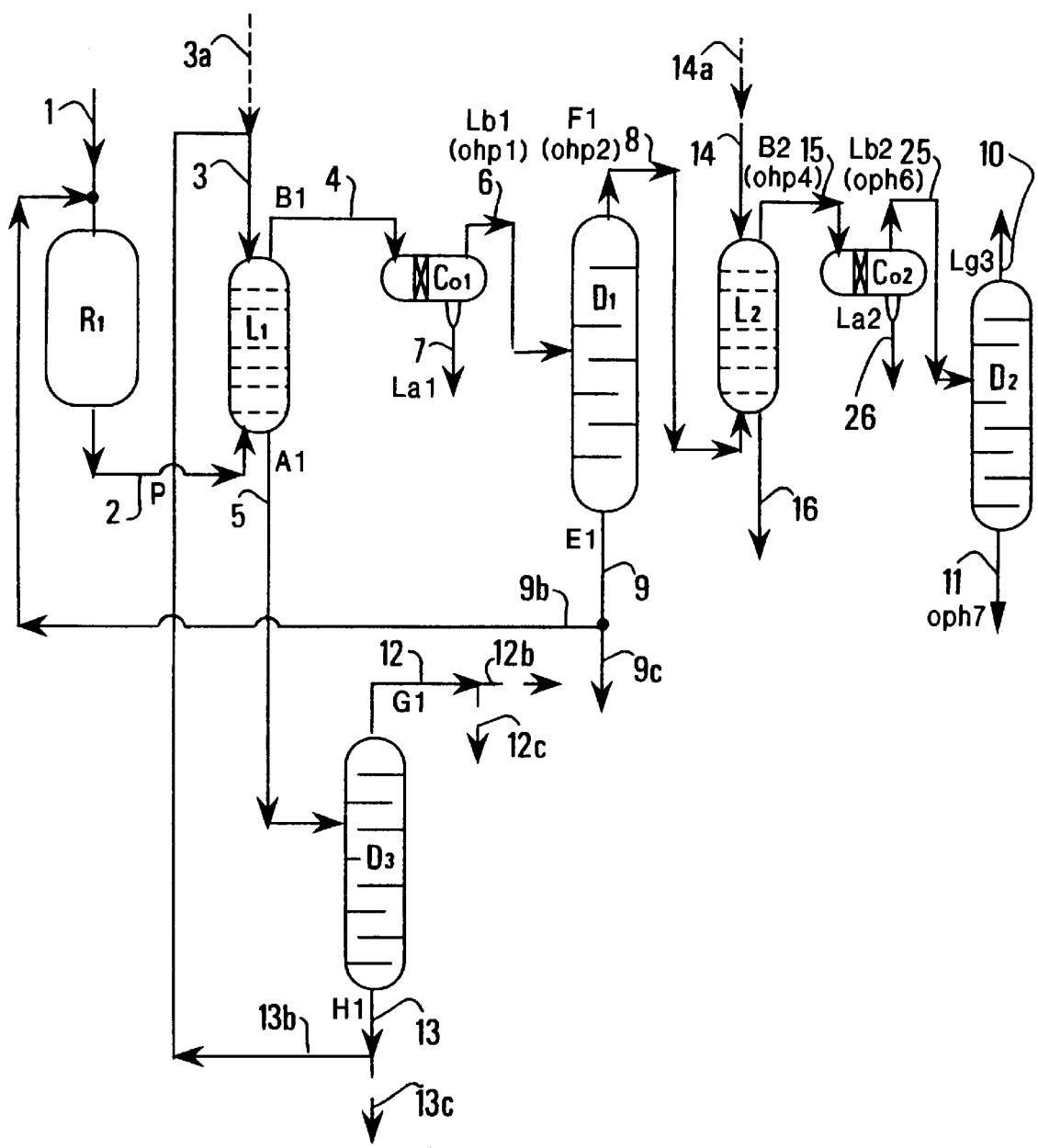
Figure 7:
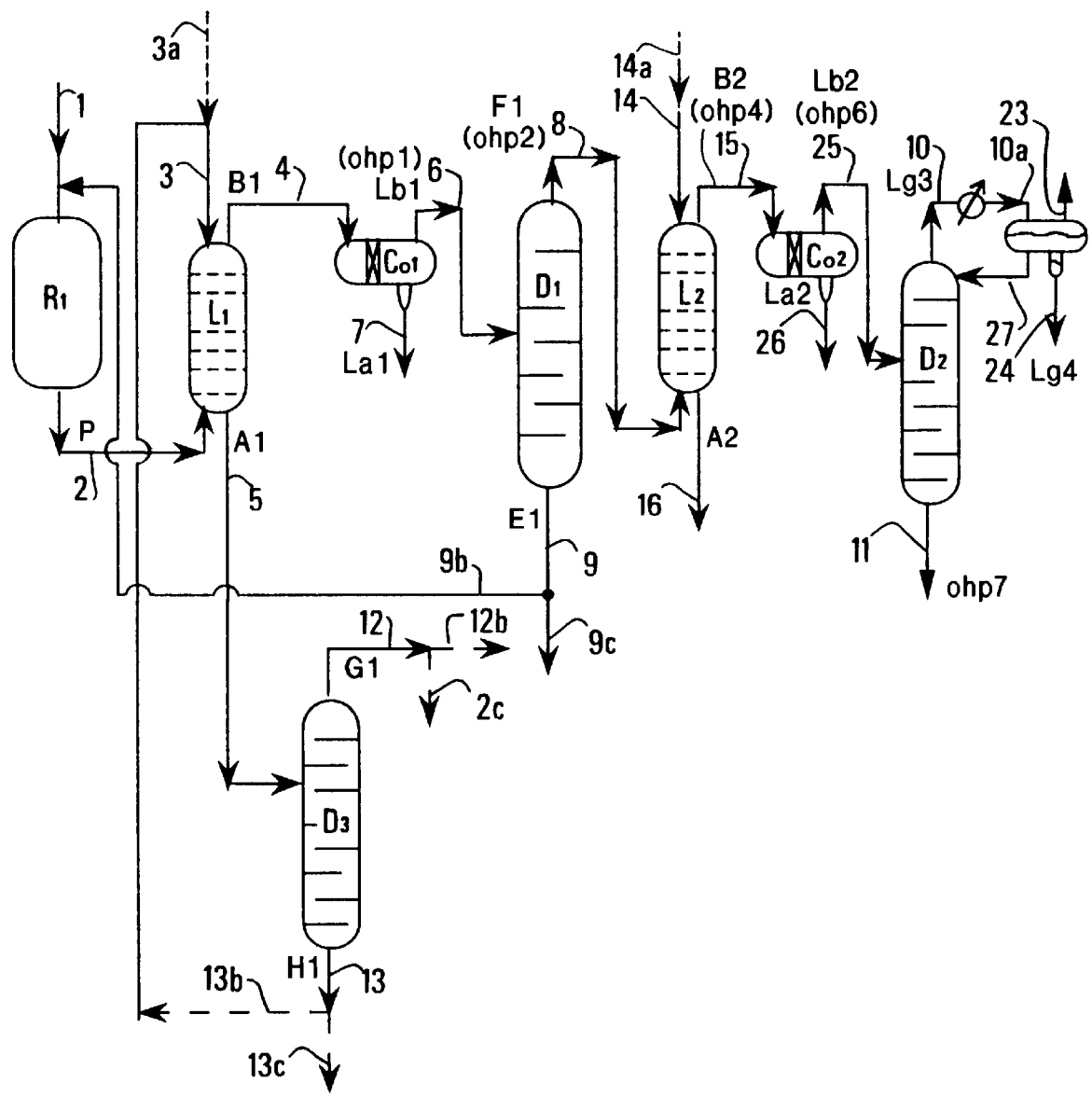

When recycling of this fraction (A2) is partial or non existent, this portion of the aqueous fraction (A2) can, for example, be sent to a waste water treatment zone via lines 16, or 16 and 16a (see FIG. 4 in particular), or 16, 16b and 16e (see FIG. 5 in particular).

In a further variation (see FIG. 5 in particular) of the process of the present invention, step f) is carried out and at least a portion of fraction (H1) from step f), for example all of the fraction, is recycled to at least one extraction zone (L1) and/or (L2), for example via lines 13, 13a and 14 to water washing extraction (L2) of step g).

In a further variation (see FIG. 5 in particular) of the process of the present invention, at least a portion of fraction (H1) from step f) is recycled to extraction zone (L1) via lines 13, 13b and 3, at least a further portion of fraction (H1) from step f) is recycled to extraction zone (L2) via lines 13, 13a and 14 and optionally, at least a further portion of fraction (H1) from step f) is purged, for example sent to a waste water treatment zone via lines 13 and 13c.

In the above variations where water is recycled to zone (L2), either from fraction (H2) from step i) or from aqueous fraction (H1) from step f), or from the two fractions, the quantity of water used in extraction zone (L2) is adjusted using at least one means for introducing makeup water via line 14a (see FIGS. 4 and 5 in particular) into zone (L2). This water makeup can compensate for loss of water due to saturation of the treated hydrocarbon stream and can replace any purged water.

In a further variation (see FIGS. 6 and 7 in particular), the process of the present invention comprises a step j) in which at least a portion of fraction (B2) from step g), preferably all of that fraction, is sent via line 15 to a separation zone (Co2) from which a liquid aqueous fraction (La2) is recovered via line 26 and a liquid organic fraction (Lb2) containing the major portion of the tertiary olefin initially present in that portion is recovered from line 25, fraction (Lb2) containing the purified tertiary olefin (Ohp6) and any light compounds.

In a yet still further variation (see FIGS. 6 and 7 in particular), the process of the present invention comprises a step k) in which at least a portion of fraction (Lb2) from step j), preferably all of that portion, is sent via line 25 to a fractionation zone (D2) from which a fraction (Lg3) containing the major portion of the light compounds initially present in that portion is recovered via line 10 and a fraction (Ohp7) containing the major portion of the tertiary olefin initially contained in that portion is recovered via line 11. Fraction (Ohp7) is essentially very pure tertiary olefin.

In one particular implementation (see FIG. 7 in particular) of the present invention, column (D2) in the various variations described above (where at least one of steps e), h) or k) is used) comprises at least one means for recovering, from fraction [Lg1-step e)-Lg2-step h) or Lg3-step k)] a substantially anhydrous fraction (Lg4), this means usually comprising a condenser into which the gaseous fraction (Lg1, Lg2 or Lg3) is introduced via line 10 and leaves, at least partially liquefied, via line 10a), to split at least part of the fraction (Lg1, Lg2 or Lg3) into a substantially anhydrous light fraction (Lg4) and an aqueous fraction which is recovered via line 94. This means is, for example, a separator drum provided with at least one means, for example a boot, for decanting and extracting an aqueous fraction. In this case the substantially anhydrous light fraction is normally split into a gaseous fraction which is evacuated via line 23 and flared off, for example, and a liquid fraction at least part of which is returned to the fractionation zone via line 27.

In a further implementation, at least part of fraction (Lg1, Lg2 or Lg3) (or substantially anhydrous light fraction (Lg4) obtained from that fraction (Lg1, Lg2 or Lg3)) is sent to a catalytic cracking zone. In a further variation, at least part of the fraction (Lg1 or Lg2 or Lg3 or Lg4) is sent to a zone for synthesising an ether by reaction between at least one alcohol and at least one tertiary olefin.

At least part, or all, of the various aqueous fractions ((La1), (H1), (A2), (H2), La2)) obtained in the various implementations of the present invention can be recycled to the washing zone (L1) when only one washing zone exists or to one or other of washing zones (L1) and (L2) when there are two washing zones, or a portion to one of them and another portion to the other.

The conditions under which step a) of the present invention are carried out are conventional tertiary alkyl ether decomposition conditions which are well known to the skilled person. In a preferred implementation, this step a) is carried out without adding supplementary water to the product introduced into the decomposition zone. However, it is possible to add a certain quantity of water, for example up to the limit of the solubility of water in the ether which is to be decomposed. Normally, the conditions under which step a) is carried out are selected so that the major portion of the tertiary alkyl ether decomposes to produce an alcohol and a tertiary olefin. In this decomposition zone, the absolute pressure is normally about 1 to about 30 bars (1 bar=0.1 MPa), preferably about 1 to about 12 bars, the temperature is normally in the range 50° C. to 300° C., preferably in the range 100° C. to 250° C., and the HSV (hourly space velocity) is normally in the range 0.1 to 200 $h^{-1}$, usually in the range 0.5 to 100 $h^{-1}$. In this zone, any of the acid catalysts known to the skilled person can be used. Solid acid catalysts are preferably used. Thus the catalyst can be selected from the group formed by acid organic resins and mineral acid resins which are generally solids under the ether decomposition reaction conditions. Of these compounds, those selected from the group formed by grafted mineral solids containing at least one alkylsulphonic, arylsulphonic or alkylarylsulphonic type organic Croup are usually used. In one preferred implementation of this step a), a catalyst selected from the group formed by polysiloxanes grafted with at least one alkylsulphonic group is used.

In step b), at least a portion of product (P) from step a) is sent to an extraction zone (L1), in which the quantity of water used for this washing is normally such that the ratio between the volume of that quantity of water introduced into the extraction zone and that of the portion of product (P) introduced into the extraction zone ($V_{water}/V_p$) is about 0.005 to about 20 by volume. This quantity of water is usually such that the ratio $V_{water}/V_p$ is about 0.005 to about 10, preferably about 0.01 to about 5, more preferably about 0.02 to about 1. Further, the water flow rate in this washing zone (L1) can also be more precisely regulated so as to maintain a foundation level in the water and alcohol fractionation zone (D3) when such a zone (D3) is present. This foundation level can be defined as the minimum level required for zone (D3) to operate properly. This parameter is a conventional parameter which is well known to the skilled person. The regulation is often carried out manually by the operators, but it is possible for this regulation to be carried out by an automatic Level Control Regulation circuit. Regardless of the selected mode of regulation, the quantity of water can generally be adjusted using a means for introducing makeup water into zone (L1). This makeup water can compensate for loss of water due to saturation of the treated hydrocarbon stream and can replace any purged water. This extraction zone (L1) is normally a tray column which operates at a temperature of about 1° C. to about 100° C., preferably about 10° C. to about 60° C. The absolute pressure in this zone is about 1 to about 20 bars, normally about 1 to about 15 bars, identical to or different from that prevailing in the fractionation zone of step b).

In step c), a zone (Co1) for separating a liquid aqueous fraction (La1) and a liquid organic fraction (Lb1) is preferably used in an apparatus termed a coalescer, in which water collects in the lower part of the apparatus by coalescence. The temperature and pressure conditions in this zone are in the same ranges as those in water extraction step b). The pressure (or respectively the temperature) can be identical to or different from that in zone (C1) of step b). In this zone, the free water contained in the product from step b) is separated out. Further, this zone also usually acts as a feed drum for the isobutene purification zone (D1) when such a zone (D1) is present. Any other means known to the skilled person can be used in the present invention. As an example, an absorbent with preferential selectivity for the aqueous or organic fraction could be used.

The general conditions for carrying out optional step d) for fractionation in a zone (D1) of at least a portion of fraction (Lb1) from step c) are selected as a function of the characteristics of the residual ether and the tertiary olefin formed. The skilled person is free to select these conditions to obtain the desired separation between a fraction containing the residual ether as its major portion and a fraction containing the olefin as its major portion. Thus, for example, in the case of MTBE decomposition and isobutene formation and where zone (D1) is a distillation column, the absolute pressure is about 1 to about 15 bars, usually about 1 to about 10 bars, identical to or different from that prevailing in zone (Co1). The column bottom temperature depends on the pressure prevailing in that column and the composition of the bottoms product. For a unit treating 1 kg/h of MTBE, the distillation zone (D1) normally comprises 3 to 80 theoretical plates, usually 5 to 50 theoretical plates.

Optional step e) for fractionating at least a portion of fraction (F1) containing the major portion of the tertiary olefin obtained from step d) in a fractionation zone (D2) can recover a fraction containing the major portion of the tertiary olefin initially present in that portion of fraction (F1) and a fraction (Lg1) containing the major portion of the light compounds initially present in that portion. The general operating conditions of step e) in the case of MTBE decomposition and isobutene formation are as follows, where zone (D2) is a distillation column: the absolute pressure is about 1 to about 15 bars, usually about 1 to about 10 bars, identical to or different from that prevailing in zone (D1). The column bottom temperature depends both on the pressure prevailing in that column and the desired purity of the tertiary olefin recovered from the column bottom. For a unit treating 1 kg/h of MTBE, the distillation zone (D2) normally comprises 2 to 80 theoretical plates, usually 3 to 60 theoretical plates.

Step f) for fractionating aqueous fraction (A1), containing the major portion of the alcohol initially present in product (P), in a zone (D3) separates that fraction (A1) into a fraction (G1) containing the major portion of the alcohol initially present in fraction (A1) and an aqueous fraction (H1) which is free of the major portion of the alcohol initially present in fraction (A1). Step f) is normally carried out in a distillation column (D3) at an absolute pressure of about 1 to about 12 bars, preferably about 1 to about 8 bars, identical to or different from that prevailing in zone (L1). The column bottom temperature depends on the pressure prevailing in that column and is normally about 50° C. to about 300° C., usually about 65° C. to about 200° C. The column normally comprises 2 to 80 theoretical plates, usually 3 to 60 theoretical plates.

In zone (L2), step g) enables purification of at least a portion of fraction (F1) from step d). The quantity of water used for water washing is normally such that the ratio between the volume of that quantity of water introduced into the extraction zone and that of the portion of fraction (F1) introduced into the extraction zone ($V_{water}/V_{F1}$) is about 0.005 to about 20 by volume. This quantity of water is usually such that the ratio $V_{water}/V_{F1}$ is about 0.005 to about 10, preferably about 0.01 to about 5, more preferably about 0.02 to about 1. The water flow rate in this washing zone (L2) can also be more precisely regulated so as to maintain a foundation level in the water and alcohol fractionation zone (D3 and/or D4) when at least one of these zones is present. This foundation level can be defined as the minimum level required for zone (D3 and/or D4) to operate properly. This parameter is a conventional parameter which is well known to the skilled person. The regulation is often carried out manually by the operators, but it is possible for this regulation to be carried out by an automatic Level Control Regulation circuit. Regardless of the selected mode of regulation, the quantity of water can generally be adjusted using a means for introducing makeup water into zone (L2). This makeup water can compensate for loss of water due to saturation of the treated hydrocarbon stream and can replace any purged water. This extraction zone (L2) is normally a tray column which operates at a temperature of about 1° C. to about 100° C. preferably about 10° C. to about 60° C. The absolute pressure in this zone is about 1 to about 20 bars, normally about 1 to about 15 bars, identical to or different from that prevailing in the fractionation zone of step b).

The general conditions for carrying out step h) for fractionating at least a portion of fraction (B2) from step g) in a zone (D2) into a liquid aqueous fraction (A2) and a liquid organic fraction (B2) are in the same ranges as those given for step g). For MTBE decomposition and isobutene formation, the temperature at the bottom of the column generally used in step h) depends both on the pressure prevailing in that column (D2) and on the desired purity of the tertiary olefin recovered from the column bottom. For a unit treating 1 kg/h of MTBE, the distillation column (D2) normally comprises between 2 and 80 theoretical plates, usually between 3 and 60 theoretical plates.

Step i) for fractionating at least a portion of the aqueous fraction (A2) containing the major portion of the alcohol initially present in fraction (F1) is carried out in a zone (D4) in which the portion of fraction (A2) is separated into a fraction (G2) containing the major portion of the alcohol initially present in fraction (A2) and an aqueous fraction (H2) which is free of the major portion of the alcohol initially present in fraction (A2). Step i) is normally carried out in a distillation column (D4) at an absolute pressure of about 1 to about 12 bars, preferably about 1 to about 8 bars, identical to or different from that in the water extraction zone of step g). The column bottom temperature particularly depends on the pressure prevailing in that column, and is normally about 50° C. to about 300° C., usually about 65° C. to about 200° C. The column normally comprises about 2 to about 80 theoretical plates, usually about 3 to about 60 theoretical plates.

Step j) can separate a liquid aqueous fraction (La2) from a liquid organic fraction (Lb2) in a separation zone (Co2). Step j) is normally carried out in an apparatus termed a coalescer, in which water collects in the lower part of the apparatus by coalescence. The temperature and pressure conditions in this zone are in the same ranges as those in zone (L2). The pressure and temperature can be identical to or different from those in zone (D2). In this zone, the free water contained in product (B2) from step g) is separated out. Further, this zone also normally acts as a feed zone or drum for an isobutene purification zone (D2) when such a zone (D2) is present. Any other means known to the skilled person can be used in the present invention. As an example, an absorbent with preferential selectivity for the aqueous or organic fraction could be used. Fraction (Lb2) contains the purified tertiary olefin (Ohp6) and possibly light compounds.

The general conditions for carrying out step k) for fractionating at least a portion of fraction (Lb2) from step j) into a light fraction (Lg3) and a liquid organic fraction (Ohp7) in a zone (D2) are selected as a function of the characteristics of the tertiary olefin formed. The skilled person will be free to select these conditions to obtain the desired separation between a fraction containing the major portion of the light compounds and a fraction containing the major portion of the olefin. Thus, in the case of MTBE decomposition and isobutene formation, for example, zone (D2) is a distillation column and the absolute pressure in that column is about 1 to about 15 bars, usually about 1 to about 10 bars, identical to or different from that prevailing in zone (Co2) of step j). The column bottom temperature depends on the pressure prevailing in that column and the composition of the bottoms product. For a unit treating 1 kg/h of MTBE, the distillation column (D2) normally comprises 3 to 80 theoretical plates, usually 5 to 50 theoretical plates.

The following example illustrates the invention without limiting its scope.

EXAMPLE 1

Figure 2:
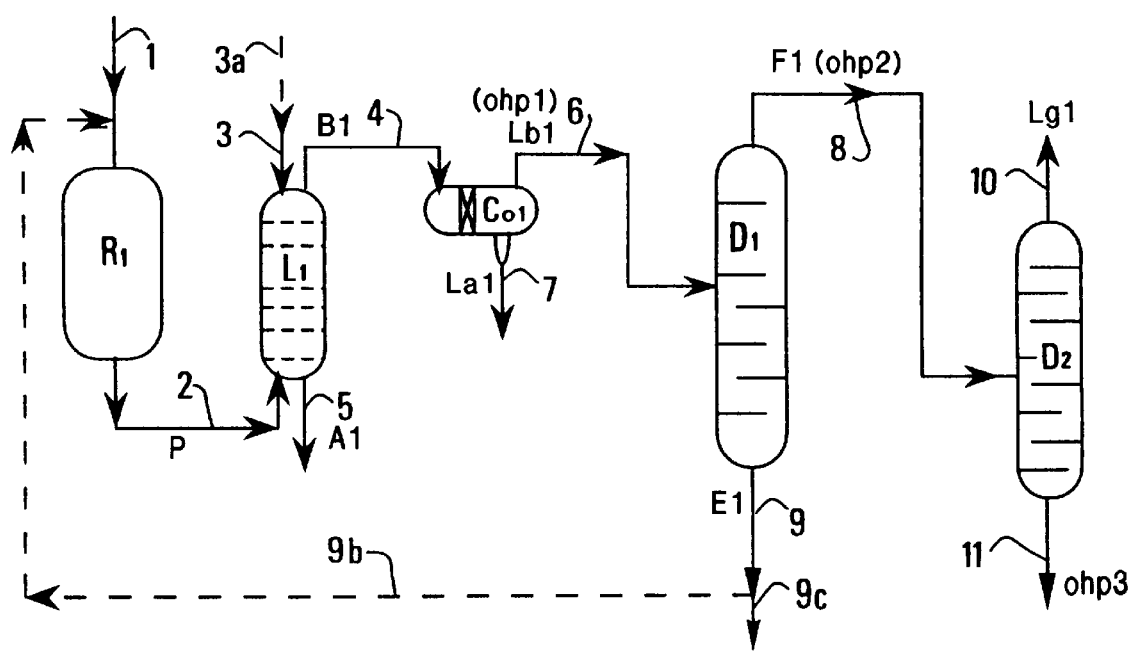
Figure 3:
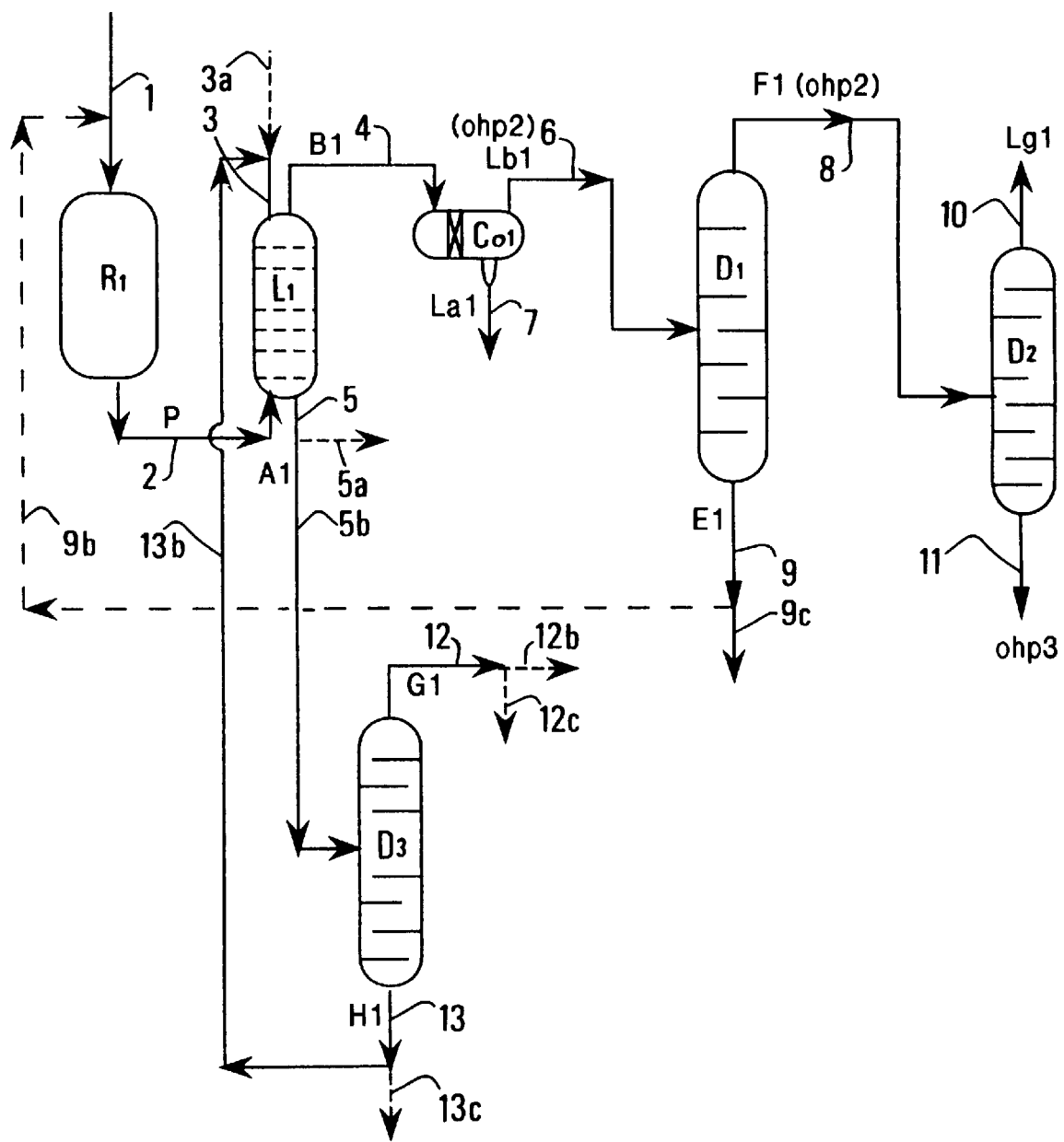
Figure 4:
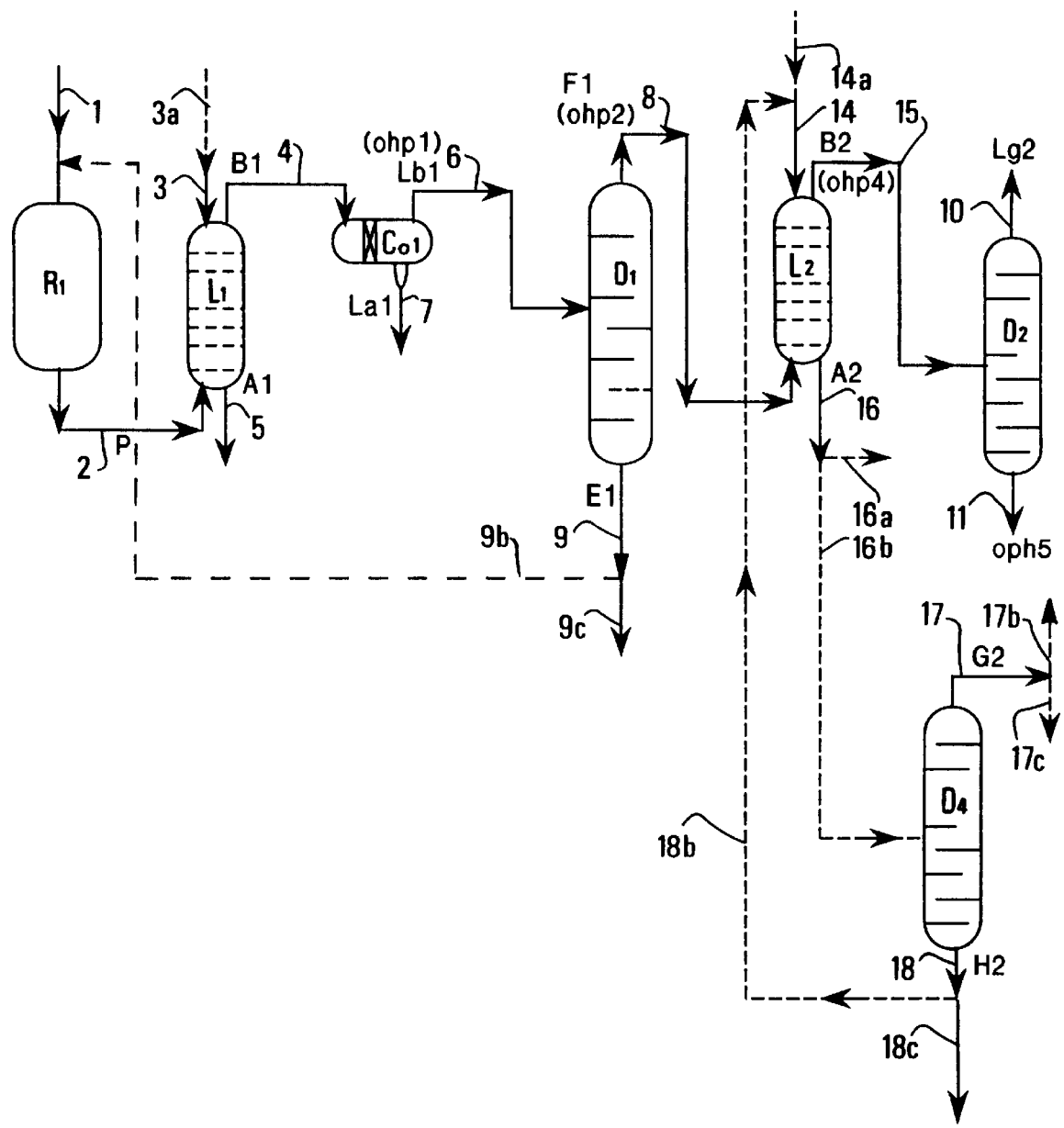

This example used the implementation shown in FIG. 2 (apart from line 9b which was not used). A pilot type unit was used which comprised a 10 ml volume tube reactor (R1), operating at a relative pressure of 7 bars, at an average to temperature of 160° C., containing 3 grams of a catalyst. The catalyst was a commercial catalyst based on polysiloxanes grafted with at least one alkylsulphonic group. Reactor (R1) was supplied with a feed containing 100% by weight of MTBE at an HSV of 15 h$^{-1}$. Table 1 shows the composition of the feed introduced into MTBE decomposition reactor (R1) and the composition of the product recovered from the outlet from reactor (R1).

TABLE 1

|  | Feed (wt %) | R1 effluent (wt %) |
|---|---|---|
| MTBE | 100 | 10 |
| Isobutene |  | 56.1 |
| Methanol |  | 32.1 |
| DME |  | 0.5 |
| Dimers |  | 1.1 |
| H$_2$O |  | 0.2 |

The various purification sections were calculated using software produced by American company SIMSCI (SIMulation SCIence INC.) under the trade name Pro II.

A water washing extraction column (L1), a tray column operating at a temperature of 30° C. at a relative pressure of 12 bars, was used in step b) of the process of the invention to obtain an aqueous fraction (A1) and an organic fraction (B1).

A coalescer tape (Co1) system for extracting free water entrained in step b) with organic fraction (B1) produced an aqueous fraction (La1) and an organic fraction (Lb1). It operated at a relative pressure of 12 bars and at a temperature of 30° C.

A distillation column (D1), operating at a relative pressure of 7 bars and comprising 20 theoretical plates, was used in step d) of the process of the invention to obtain a bottoms product (E1) and an overhead product (F1).

A distillation column (D2), the last step in the isobutene purification, operating at a relative pressure of 7 bars and comprising 20 theoretical plates, was used in step e) of the process of the invention to obtain a bottoms product (Ohp3) which was purified isobutene and an overhead product (Lg1) containing light compounds.

The water washing extraction column (L1) was supplied with effluent (P) from (R1). An aqueous fraction (A1) containing the majority of the methanol contained in product (P) from reactor (R1) was recovered from the bottom of this column and an organic fraction (B1) containing the majority of the isobutene formed in reactor (R1) was recovered overhead. Product (B1), also containing a small quantity of entrained water from the water washing zone (L1), was sent to a coalescer (Co1) type free water extraction system, from which water was eliminated by decanting. An essentially organic fraction (Lb1) was also recovered from this system. This fraction (Lb1) was sent to a distillation column (D1) from which a fraction (E1) containing principally ether which had not decomposed in reactor (R1) was recovered from the bottom and a fraction (F1) containing principally isobutene was recovered overhead. Fraction (F1) was sent to column (D2) from which a light fraction (Lg1) containing DME (dimethylether) was recovered overhead and a high purity isobutene fraction (Ohp3) was recovered from the bottom.

The material balances are shown in Tables 2 and 3 below.

TABLE 2

|  | Effluent from reactor (R1) (wt %) | Washing water column (L1) | Aqueous fraction (A1) (g/h) | Organic fraction (B1) (g/h) | Aqueous fraction (La1) (g/h) | Organic fraction (Lb1) (g/h) |
|---|---|---|---|---|---|---|
| MTBE | 10 |  |  | 10 |  | 10 |
| Isobutene | 56.1 |  |  | 56.1 |  | 56.1 |
| Methanol | 32.1 |  | 32 | 0.1 |  | 0.1 |
| DME | 0.5 |  |  | 0.5 |  | 0.5 |
| Dimers | 1.1 |  |  | 1.1 |  | 1.1 |
| H$_2$O | 0.2 | 50 | 48 | 2.2 | 2.1 | 0.1 |
| Flow rate (g/h) | 100 | 50 | 80 | 70 | 2.1 | 67.9 |

TABLE 3

|  | Fraction (F1) overhead from (D1) | Fraction (E1) bottom of (D1) | Fraction (Lg1) column (D2) | Fraction (Ohp3) column (D2) |
|---|---|---|---|---|
| MTBE |  | 10 |  |  |
| Isobutene | 56.1 |  | 1.6 | 54.5 |
| Methanol | 0.1 |  | 0.1 |  |
| DME | 0.5 |  | 0.45 | 0.05 |
| Dimers |  | 1.1 |  |  |
| H$_2$O | 0.1 |  | 0.1 |  |
| Flow rate (g/h) | 56.8 | 11.1 | 2.25 | 54.55 |
| Isobutene purity (%) |  |  |  | >99.9% |

Thus the isobutene produced by the process of the invention was of very high purity.

This was a pilot type apparatus comprising a tube reactor R1 operating at a relative pressure of 7 bars, and at an average temperature of 140° C. Reactor R1 contained Deloxan ASP (a catalyst which is a polysiloxane grafted with alkylsulphonic groups). R1 was supplied with a feed containing 100% by weight of TAME at a HSV of 6 h$^{-1}$. The product recovered from the R1 outlet had the composition given in Table 4:

TABLE 4

TAME DECOMPOSITION REACTION SECTION

|  | Feed (wt %) | R1 effluent (wt %) |
|---|---|---|
| TAME | 100 | 15 |
| Isoamylenes |  | 58.2 |
| Methanol |  | 26.45 |
| DME |  | 0.25 |
| Dimers |  | 0.1 |

As in the preceding example, the purification sections were calculated using Pro II software, using the specifications required for each of the outlet streams.

We shall content ourselves here with providing a summary material balance (Table 5) to illustrate one implementation of our process (analogous flowsheet to that of Example 1 illustrated in FIG. 2, using the second purification column D2).

TABLE 5

|  | Effluent R1 | Washing water | Aqueous fraction A1 | Organic fraction B1 | Organic fraction Lb1 | Fraction F1 head of D1 |
|---|---|---|---|---|---|---|
| TAME | 15 | | | 15 | 15 | |
| Iso-amylenes | 58.2 | | | 58.2 | 58.2 | 58.2 |
| Methanol | 26.45 | | 26.4 | 0.05 | 0.05 | 0.05 |
| DME | 0.25 | | | 0.25 | 0.25 | 0.25 |
| Dimers | 0.1 | | | 0.1 | 0.1 | |
| $H_2O$ | | 40 | 38 | 2 | 0.1 | 0.1 |
| Flow rate (g,h) | 100 | 40 | 64.4 | 75.6 | 73.7 | 58.6 |

Isoamylenes were thus produced with a minimum yield of 84% (the yield could be improved by recycling unconverted ether, for example as illustrated in FIG. 2) and with a purity of over 99%.

We claim:

1. A process for producing a tertiary olefin by decomposing a tertiary alkyl ether, comprising:
    a) decomposing at least one tertiary alkyl ether in a reaction zone comprising at least one reactor (R1) containing a catalyst for decomposing said ether, under conditions which can at least partially decompose said tertiary alkyl ether to a product (P) containing at least one alcohol and at least one tertiary olefin and optionally ether which has not been decomposed in step a) and optionally light compounds;
    b) purifying at least a portion of product (P) in a water washing extraction zone (L1) to obtain an aqueous fraction (A1) containing most of the alcohol present in and a fraction (B1) containing most of the tertiary olefin initially present in said portion, said fraction (B1) containing said tertiary olefin, water, optionally ether and optionally light compounds and being substantially free of alcohol;
    said process further comprising step c) comprising passing at least a portion of fraction (B1) from step b) to a separation zone (Co1), to recover a liquid aqueous fraction (La1) and a liquid organic fraction (Lb1) containing most of the tertiary olefin initially present in said portion of the fraction (B1), said fraction (Lb1) containing said tertiary olefin, optionally ether and optionally light compounds, said fraction (Lb1) being depleted of water.

2. A process according to claim 1, in which at least a portion of the liquid aqueous fraction (La1) obtained from step c) is recycled to zone (L1).

3. A process according to claim 1, further comprising a step f) of passing at least a portion of fraction (A1) to a fractionation zone (D3) to recover a fraction (G1) containing most of the alcohol initially present in said portion of fraction (A1) and an aqueous fraction (H1) which is free of most of the alcohol initially present in said portion of fraction (A1).

4. A process according to claim 3, in which at least a portion of fraction (G1) is sent to a zone for synthesising ether by reaction between at least one alcohol and at least one tertiary olefin.

5. A process according to claim 3, in which at least a portion of the aqueous fraction (H1) is recycled to zone (L1).

6. A process according to claim 1, further comprising introducing makeup water into zone (L1).

7. A process according to claim 1, further comprising a step d) of passing at least a portion of the organic fraction (Lb1) to a fractionation zone (D1) to recover a fraction (E1) containing most of the ether initially contained in said portion of the organic fraction (Lb1) and a fraction (F1) containing most of the tertiary olefin initially contained in said portion of (Lb1).

8. A process according to claim 7, in which at least a portion of the fraction (E1) is recycled to zone (R1).

9. A process according to claim 7, comprising a step e) of passing at least a portion of fraction (F1) to a fractionation zone (D2) to recover a fraction (Lg1) containing most of any light compounds initially present in said portion of (F1) and a fraction (Ohp3) containing most of the tertiary olefin initially contained in said portion of (F1).

10. A process according to claim 7, comprising a step g) of passing at least a portion of fraction (F1) to a water washing extraction (L2) to recover an aqueous fraction (A2) containing most of the alcohol initially present in said portion of (F1) and a fraction (B2) containing most of the tertiary olefin initially present in said portion of (F1).

11. A process according to claim 10, comprising a step h) of passing at least a portion of organic fraction (B2) to a fractionation zone (D2) to recover a fraction (Ohp5) containing most of the tertiary olefin initially present in said portion of (B2) and a fraction (Lg2) containing most of any light compounds initially present in said portion of (B2).

12. A process according to claim 10, comprising a step i) of passing at least a portion of the aqueous fraction (A2) from step g) to a fractionation zone (D4) to recover a fraction (G2) containing most of the alcohol initially present in said portion of (A2) and an aqueous fraction (H2) which is free of most of the alcohol initially present in said portion of (A2).

13. A process according to claim 12, in which at least a portion of the fraction (G2) is sent to a zone for synthesising ether by reaction between at least one alcohol and at least one tertiary olefin.

14. A process according to claim 12, in which at least a portion of aqueous fraction (H2) is recycled to at least one water extraction zone, (L1) and/or (L2).

15. A process according to claim 10, in which at least a portion of the aqueous fraction (A2) is recycled to zone (L1).

16. A process according to claim 10, further comprising a step f) of passing at least a portion of fraction (A1) to a fractionation zone (D3) to recover a fraction (G1) containing most of the alcohol initially present in said portion of (A1) and an aqueous fraction (H1) which is free of most of the alcohol initially present in said portion of (A1) and at least a portion of the aqueous fraction (A2) is sent to the fractionation zone (D3) of step f).

17. A process according to claim 10, further comprising a step f) of passing at least a portion of fraction (A1) to a fractionation zone (D3) to recover a fraction (G1) containing most of the alcohol initially present in said portion of (A1) and an aqueous fraction (H1) which is free of most of the alcohol initially present in said portion of (A1) and at least a portion of the aqueous fraction (A2) is sent to the fractionation zone (D3) of step f).

18. A process according to claim 10, further comprising introducing makeup water into zone (L2).

19. A process according to claim 10, comprising a step j) in which at least a portion of fraction (B2) from step g) is sent to a separation zone (Co2) from which a liquid aqueous fraction (La2) and a liquid organic fraction (Lb2) containing the major portion of the tertiary olefin initially present in said portion are recovered, said fraction (Lb2) containing said purified tertiary olefin and any light compounds.

20. A process according to claim 19, comprising a step k) in which at least a portion of fraction (Lb2) from step j) is sent to a fractionation zone (D2) from which a fraction (Ohp7) containing the major portion of the olefin initially present in said portion and a fraction (Lg3) containing the majority of the light compounds initially present in said fraction (Lb2) are recovered.

21. A process according to claim 9, wherein the fractionation zone (D2) from which a fraction (Lg1, or Lg2 or Lg3) is recovered comprises at least one means for obtaining a substantially anhydrous light fraction (Lg4).

22. A process according to claim 21, in which said means for obtaining said fraction (Lg4) comprises at least one condenser for condensing at least a portion of the fraction (Lg1 or Lg2 or Lg3).

23. A process according to claim 21, in which said means can recover an aqueous fraction and recycle a liquid organic fraction to said fractionation zone (D2).

24. A process according to claim 21, in which at least part of said fraction (Lg4) is sent to a zone for synthesising ether by reaction between at least one alcohol and at least one tertiary olefin.

25. A process according to claim 9, wherein at least part of the fraction (Lg1 or Lg2 or Lg3) from the fractionation zone (D2) is sent to a zone for synthesising ether by reaction between at least one alcohol and at least one tertiary olefin.

26. A process according to claim 11, wherein the fractionation zone (D2) from which a fraction (Lg1 or Lg2 or Lg3) is recovered comprises at least one means for obtaining a substantially anhydrous light fraction (Lg4).

27. A process according to claim 20, wherein the fractionation zone (D2) from which a fraction (Lg1 or Lg2 or Lg3) is recovered comprises at least one means for obtaining a substantially anhydrous light fraction (Lg4).

28. A process according to claim 11, wherein at least part of the fraction (Lg1 or Lg2 or Lg3) from the fractionation zone (D2) is sent to a zone for synthesising ether by reaction between at least one alcohol and at least one tertiary olefin.

29. A process according to claim 20, wherein at least part of the fraction (Lg1 or Lg2 or Lg3) from the fractionation zone (D2) is sent to a zone for synthesising ether by reaction between at least one alcohol and at least one tertiary olefin.

30. A process according to claim 1, wherein the separation zone (Co1) of step is a totally liquid phase zone.

31. A process according to claim 1, wherein the separation zone (Co1) of step is a coalescing zone.

* * * * *